United States Patent
Pivonka et al.

(10) Patent No.: US 8,504,138 B1
(45) Date of Patent: Aug. 6, 2013

(54) METHOD OF MAKING AND USING AN APPARATUS FOR A LOCOMOTIVE MICRO-IMPLANT USING ACTIVE ELECTROMAGNETIC PROPULSION

(75) Inventors: Daniel Michael Pivonka, Stanford, CA (US); Ada Shuk Yan Poon, San Leandro, CA (US); Teresa H. Meng, Saratoga, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 873 days.

(21) Appl. No.: 12/485,654

(22) Filed: Jun. 16, 2009

(51) Int. Cl.
*A61B 1/00* (2006.01)

(52) U.S. Cl.
USPC .......................... 600/411; 600/410; 600/407

(58) Field of Classification Search
USPC .......................................... 600/411, 410, 407
See application file for complete search history.

(56) References Cited

U.S. PATENT DOCUMENTS 6,517,477 B1 * 2/2003 Wendlandt .................... 600/114
2010/0298635 A1 * 11/2010 Hata et al. ..................... 600/104

OTHER PUBLICATIONS

Ada S.Y. Poon, et al., "Optimal Frequency for Wireless Power Transmission into Dispersive Tissue", Annual International Conference of the IEEE Engineering in Medicine and Biology Society, Lyon, France, Aug. 2007, pp. 1-12.

* cited by examiner

Primary Examiner — Long V. Le
Assistant Examiner — Farshad Negarestan
(74) Attorney, Agent, or Firm — Pillsbury Winthrop Shaw Pittman LLP

(57) ABSTRACT

The present inventions provide a locomotive implant for usage within a predetermined magnetic field that includes a capsule body; a wireless power receiver disposed within the capsule body; a plurality of switchable conductors having a predetermined pattern within the capsule body, each of the switchable conductors adapted to pass a current along a forward path to thereby create, in the presence of the predetermined magnetic field, a force and assist in moving the locomotive implant; and a controller adapted to receive directional control signals to control the switchable current wires or conductors. Methods of using the same are described.

23 Claims, 8 Drawing Sheets

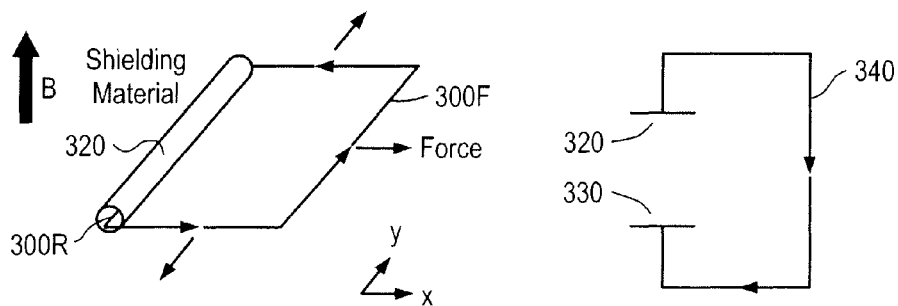
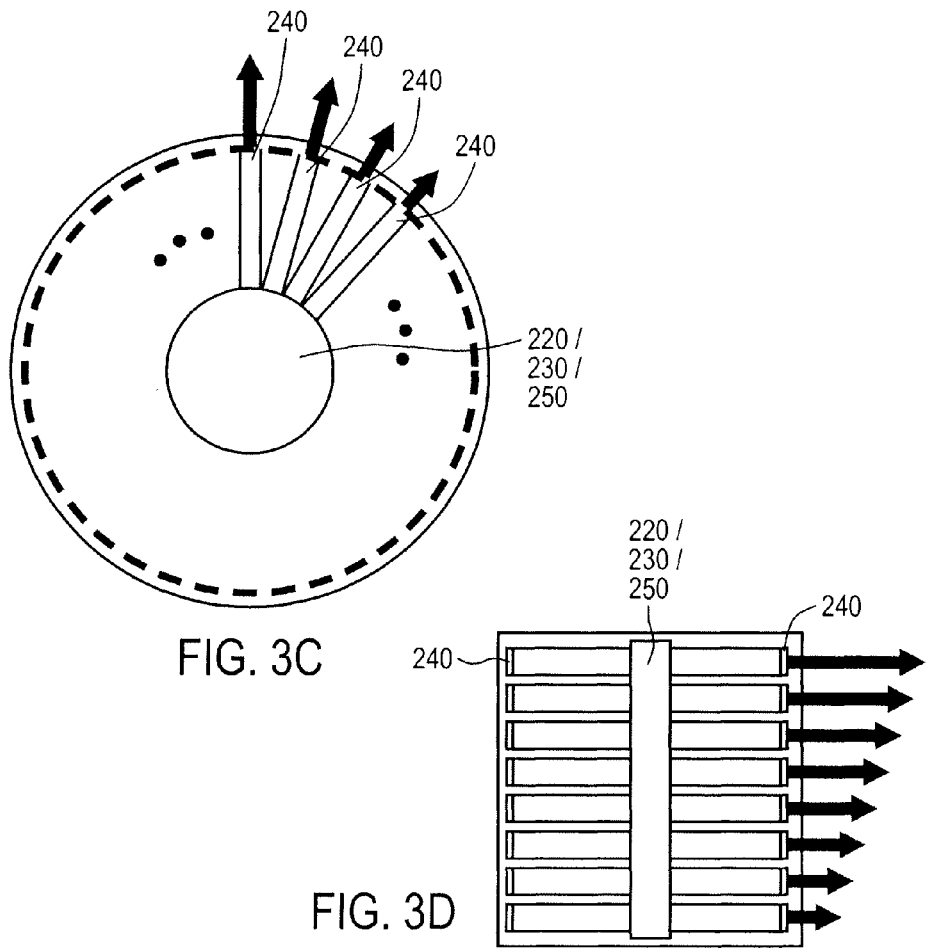

METHOD OF MAKING AND USING AN APPARATUS FOR A LOCOMOTIVE MICRO-IMPLANT USING ACTIVE ELECTROMAGNETIC PROPULSION

FIELD OF THE INVENTIONS

The present inventions relate to methods of making and using an apparatus for a locomotive micro-implant using active electromagnetic propulsion.

BACKGROUND

Locomotive implantable devices have numerous applications including sensing, imaging, minimally invasive surgery, and research. Many techniques have been used to generate motion, including mechanical solutions and passive magnetic solutions. Power sources dominate the size of existing active implant technologies, and this size constraint (typically in the cm-range) limits the potential for propulsion. Additionally, mechanical propulsion is inherently inefficient at the scale of interest.

Passive locomotion schemes have circumvented the power and efficiency issues, but require large field gradients and usually cannot generate vertical motion. In a passive magnetic propulsion technique, a force is exerted on a small ferromagnetic material with magnetic field gradients. The passive propulsion method typically employs MRI-like systems because the gradient fields must be large and precisely controlled. The gradient must be in the direction of movement, and even MRI systems cannot overcome the force of gravity for devices smaller than roughly 1 mm. The force scales poorly as the size is reduced because it is proportional to the volume of the object. From a practical perspective, generating large field gradients is complicated, and current technology is inadequate.

In addition to the passive method, it is also possible to use mechanical propulsion with active power. Mechanical propulsion is accomplished with a wide variety of techniques. A few possible methods include flagella/motors, pumps, and acoustic streaming. These designs typically suffer from low conversion efficiency from input power to thrust, especially as the Reynolds number decreases. There are losses associated with the conversion from electrical power to mechanical motion, and more loss associated with the conversion from mechanical motion to forward thrust. As a result of the low efficiency, a fairly substantial amount of power is required, and the power source dominates the size making it difficult to miniaturize.

SUMMARY

The present inventions relate to methods of making and using an apparatus for a locomotive micro-implant using active electromagnetic propulsion.

The present inventions provide a locomotive implant for usage within a predetermined magnetic field that includes a capsule body; a wireless power receiver disposed within the capsule body; a plurality of switchable conductors having a predetermined pattern within the capsule body, each of the switchable conductors adapted to pass a current along a forward path to thereby create, in the presence of the predetermined magnetic field, a force and assist in moving the locomotive implant; and a controller adapted to receive directional control signals to control the switchable current wires or conductors.

Methods of using the same are described.

BRIEF DESCRIPTION OF THE DRAWINGS

These and other aspects and features of the present invention will become apparent to those of ordinary skill in the art upon review of the following description of specific embodiments of the invention in conjunction with the accompanying figures, wherein:

FIGS. 3(a)-(d) illustrate various embodiments of a current flow mechanism within a locomotive implant;

DETAILED DESCRIPTION OF THE PREFERRED EMBODIMENTS

Described herein is a new locomotive implant device, and related method, for controlling the same, which can enhance functionality for a variety of applications, as well as provide new applications, as described herein. The locomotive implant as described hereinafter can be remotely powered, remotely controlled, capable of sending and receiving data, and is highly adaptable.

This locomotive implant device uses active electromagnetic propulsion, which has many advantages over the methods mentioned above. It can efficiently generate thrust with a static magnetic field. The motion is highly controllable with simple manipulations of currents, and the gravitational forces can be balanced with buoyant forces with minor adjustments. Thus, active electromagnetic propulsion offers the flexibility to meet the requirements of a variety of applications, whether they require small sizes or small magnetic fields, as described in more detail herein below.

Usage of improved wireless power transmission efficiency allows for mm-sized locomotive implants, as described herein, to receive on the order of 150 µW at a depth of 2 cm, which is sufficient to develop the necessary propulsion.

The electromagnetic propulsion technique described herein is preferably the development of a Lorentz force on specific wire arrangements. In addition to forward propulsion, these wire arrangements can generate torques to steer the device through a fluid, which fluid, as described herein, can be a liquid fluid or a gaseous fluid.

Although the magnetic field only exerts perpendicular forces on the wires, altering the orientation of the locomotive implant, as described hereinafter, can generate lift due to the fluid drag force, resulting in vertical motion. It is also possible to alter the orientation of the external magnetic field to directly generate forces in any direction. This magnetic field can be static, or it can be an oscillating field that is synchronized with the currents on the device.

Figure 1:
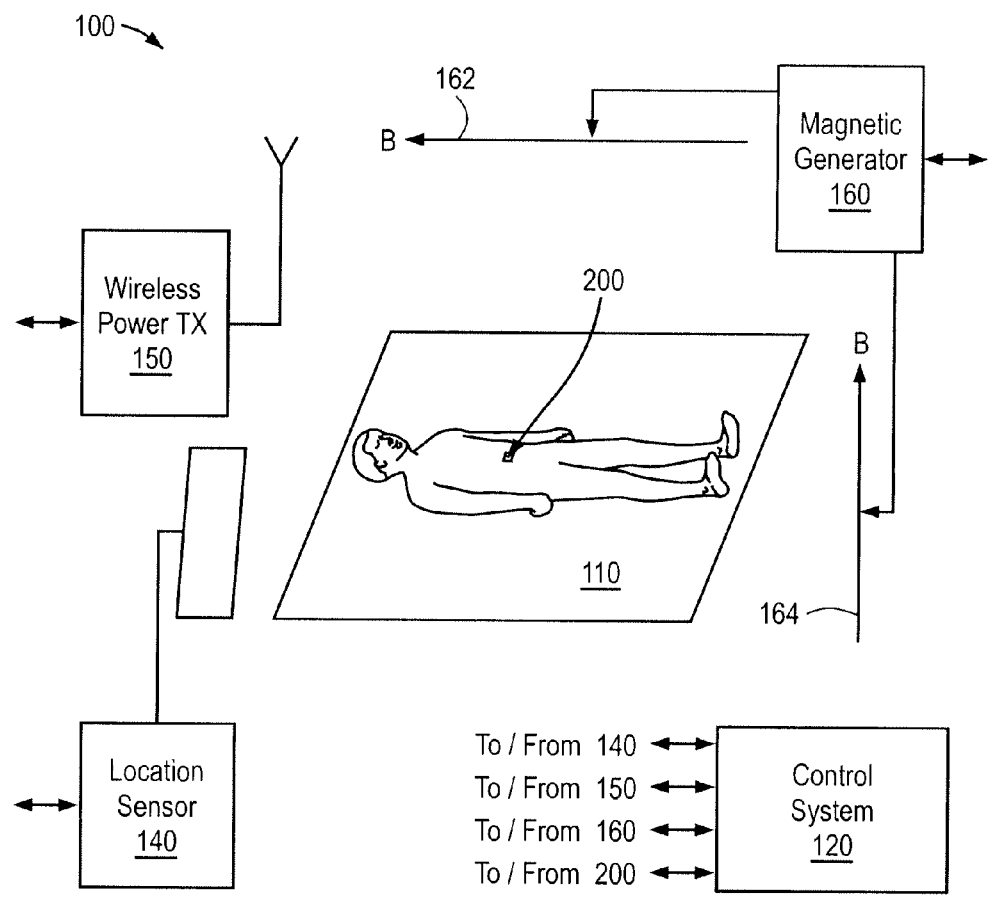
FIG. 1 illustrates a system diagram of one embodiment of a locomotive implant system.

FIG. 1 illustrates a system diagram of one embodiment of a locomotive implant system 100. As shown, there exists an area 110 on which a live person 120 is disposed, though the present invention can operate with other animal species, as well as in and with other non-living environments, such as plumbing systems, pumps, compressors, other industrial equipment, mobile smart dust/sensors (like Berkeley motes, but with motion). Within the area 110 is a central control system 120, which contains a processor, memory and other well-known computer functions, in order to execute the functionality described herein, typically in the form of application software written to monitor the power and magnetic fields as described herein, as well as monitor the locomotive implant described herein, in order to control the transmitted power, the applied magnetic field, as well as the various mechanisms described herein that exist within the locomotive implant, to thereby control the movement of the locomotive implant with the body 120 of the person.

As shown, there exists a location sensor 140, which receives control signals from the central control system 120, and which essentially provides signals that can be used to detect the specific and precise position of the locomotive implant 200 within the body 120. The location sensor can be an imaging apparatus that detects the presence of the locomotive implant based upon some characteristic of the locomotive implant 200, such as the mutual inductance of the link, electromagnetic absorption, temperature difference, or scattered field from the implant. Alternatively, the location sensor 140 can be a separate imaging system such as ultrasound or MRI, or it can be based on data transmitted from the device. In each of these embodiments, precise position information is provided to the central control system 120.

Wireless power transmitter 150 is shown as well, which power transmitter transmits RF power to a power receiver disposed within the locomotive implant 200. The power transfer characteristics of the wireless power transmitter 150 are controlled by the central control system 120. The wireless power receiver within the locomotive implant is described hereinafter.

Also illustrated is the magnetic field generator 160, which is able to generate magnetic fields, preferably in two orthogonal directions, such as 162 and 164 as shown in FIG. 1, in order to allow for three directional movement as described herein. The magnetic field generator can be implemented simply using a permanent magnet or with electromagnets.

Figure 2:
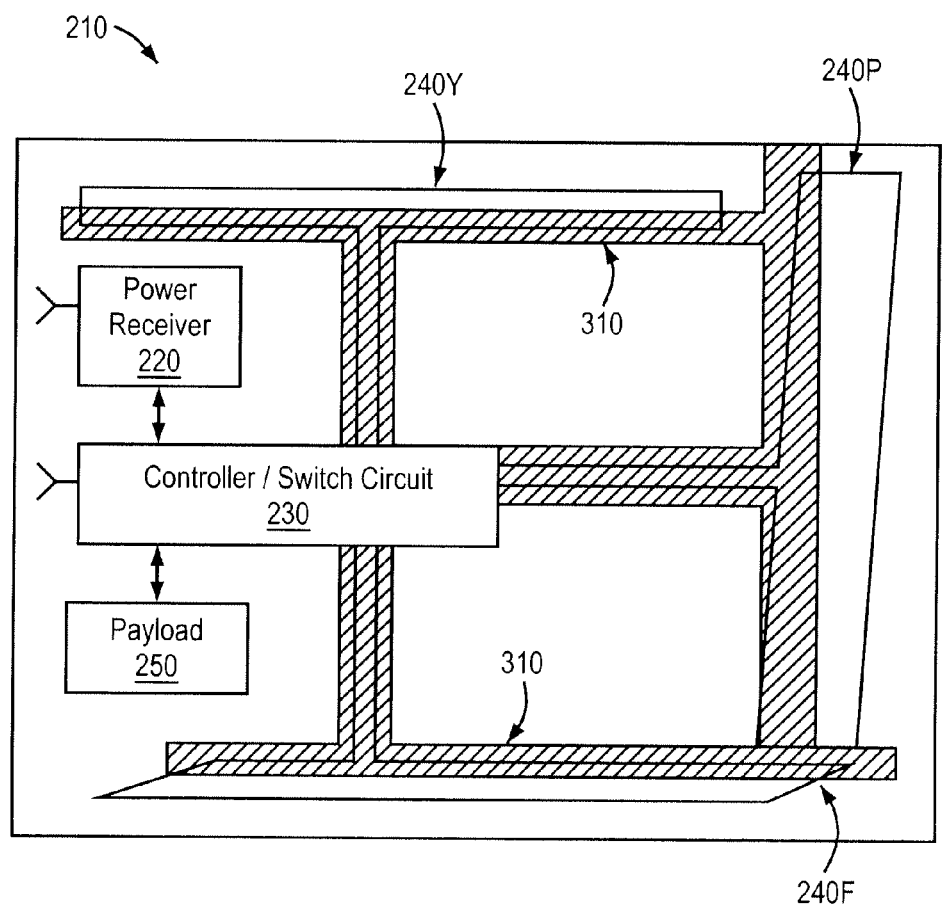
FIG. 2 illustrates a block diagram of a locomotive implant according to one embodiment
Figures 4A, 4B, 4C, 4D:
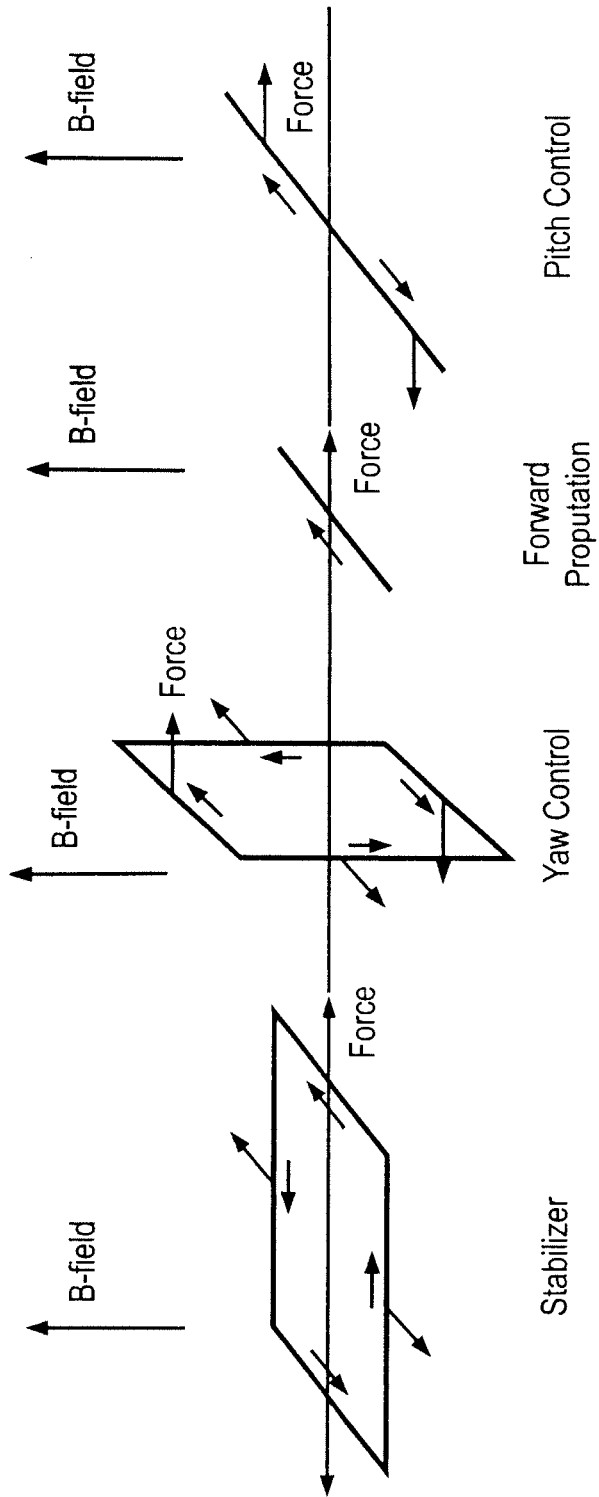
FIG. 4(a) illustrates a loop current orthogonal to the magnetic field that provides a stabilizing force.
FIG. 4(b) illustrates a loop current parallel to the magnetic field that provides a stabilizing force.
FIG. 4(c) illustrates a unidirectional linear current orthogonal to the magnetic field that provides a forward force.
FIG. 4(d) illustrates a bi-directional linear current orthogonal to the magnetic field that provides a pitch control force.

FIG. 2 illustrates a block diagram of a circuit 210 that is used within the locomotive implant 200, according to one embodiment, which does not include the enclosure material and other physical design aspects discussed hereinafter.

With respect to FIG. 2, overall there exist four different primary components to the circuit 210: the power receiver 220, the locomotive implant controller 230, switchable conductors 240, and the payload 250, each of which will be discussed in more detail hereinafter.

The power receiver 220 receives power for the locomotive implant circuit 210.

In one embodiment, the power receiver 210 receives the transmitted radio frequency power signal from the wireless power transmitter 150, and converts this RF signal into electrical power. This mechanism for the power reception, as well as the further down-conversions necessary to obtain usable electrical power, is described in further detail in U.S. patent application Ser. No. 12/485,641 filed on the same day as this application, and which is entitled "Wireless Power Transmission For Implantable Medical Devices" the contents of which are expressly incorporated by reference herein.

In another embodiment in which the locomotive implant 200 is connected to another device, in order to control certain movements of the other device as described hereafter, the power receiver 220 can be wired, in which case the power receiver 220 can be implemented with essentially a wire.

The locomotive implant controller 230 receives control signals from the central control system 120 in order to control which ones of the switchable conductors 240 are turned on at any given time, in order for the appropriate motion to occur, as described further hereinafter. With respect to FIG. 2, there is shown, in simplification, an implementation of the switchable conductors implemented as a pattern with three conductive loops 240Y, 240P and 240F, which are loosely akin to Yaw, Pitch and Forward movement control, which can be used to generate movement in a desired direction, as described further hereinafter, as well as are depicted the shield regions 310 over a return length of the conductive loops as well as a routing length between the conductive loop and the control system 120, the purpose of the shield regions 310-being described hereinafter. It is understood that various arrangements of conductors 240, within the presence of the known magnetic field and a predetermined current, will provide a contribution to the overall force for movement of the implant 200, and that as such complicated structures of conductors 240 can be created to enhance movement as desired.

In certain embodiments, the locomotive implant controller 230 can also receive payload control signals, to control what to do with a payload 250, if any. Before discussing payloads, it should also be recognized that the locomotive implant controller 230 can also transmit control signals back to the central control system 120. Such control signals can be used to assist in providing for the location of the locomotive implant 200 within the body 120, and also can be used to indicate that each of the different components is operating properly. In one embodiment, if for some reason one of the switchable conductors 240 is malfunctioning, implant controller 230 can indicate such malfunction to the central control system 120, which can then determine alternative combinations of switchable conductors 240 to use to obtain a substantially equivalent force as needed for movement of locomotive implant 200.

FIGS. 3(a)-(d) illustrate various embodiments of current flow mechanisms within a locomotive implant circuit 210 that can be used to generate movement of the locomotive implant. FIGS. 3(a) and 3(b) illustrate different mechanisms within a single switchable conductor 240 that is implemented as a loop, whereas FIGS. 3(b) and 3(c) show embodiments in which a great many differently switchable conductors 240, each configured as loops, are included in order to provide for more precise as well as redundant control, as described.

As an overview, before discussing specific current-flow mechanisms, a discussion of force generation and fluid motion is provided. For the purposes of this analysis, buoyant forces and gravitational forces are not considered. The force F on a current-carrying wire is simply $$F = IL \times B, \quad (1)$$

where I is the current in the wire, L is a vector denoting the length and direction of the wire, and B is the magnetic field. This force is always perpendicular to the magnetic field, and is maximized when the wire orientation is perpendicular to the field.

To generate a forward force with a loop of wire 300, the force on the return path 300R for the current must be less than the force on the forward path 300F.

FIG. 3A illustrates on embodiment in which a uniform conductor is used to make the loop 300, and the return path 300R is shielded from the magnetic field using a magnetic shielding material 310, such as a mu-metal. Thus, the currents in the return path 300R are prevented from experiencing forces.

In another embodiment, now shown, instead of using a shield material 310 over a return path, different conductive materials with different permeability are used for the forward path 300F and the return path 300R, which provides the equivalent effect through field amplification instead of field attenuation.

In another embodiment, illustrated in FIG. 3B, two electrodes at different high potential 320 and low potential 330 are used, such that there exists only single "forward" path 340.

With respect to either of the above-described implementations, The forces in the y-direction cancel, and the net force in the x-direction is $$F=(1-\alpha)ILB, \quad (2)$$

where $\alpha$ represents the attenuation of the field inside the shielding material. When $\alpha$ is zero, the shielding is perfect and the wire inside the shielding material exerts no force on the device. Maximizing the force can be accomplished by maximizing I and L. The power consumption P of the main force generating wire is $$P = I^2 R = I^2 \rho_c \frac{L}{A_W}, \quad (3)$$

where R is the resistance, $\rho_c$ is the conductivity, and $A_w$ is the cross-sectional area of the wire. The total power of the device is the sum of the power consumed by the wires plus the power consumed by the other components described. Equations (2) and (3) define the tradeoff between power consumption and the thrust force. Decreasing I and increasing L by the same factor results in the same force with less power usage. Also, increasing $A_w$ reduces the required power. Therefore, the L and $A_w$ should be maximized to achieve the best performance.

The thrust force works against the fluid drag force, which is velocity dependent. The dependence on velocity changes with the Reynolds number. The Reynolds number is given as $$Re = \frac{\rho_f v D}{\mu}, \quad (4)$$

where $\rho_f$ represents the density of the fluid, v is the velocity of the object, D is a characteristic dimension, and $\mu$ is the viscosity of the fluid. As the locomotive implant 200 becomes smaller, the Reynolds number decreases. For Reynolds numbers much greater than one (typically larger than 1000), the drag force $D_1$ can be written as $$D_1 = \frac{1}{2}\rho_f v^2 A_f C_{D_1} \quad (5)$$

where $\rho_f$ is the density of the fluid, v is the velocity, $A_f$ is the frontal area of the device, and $C_D$ is the drag coefficient. When the two forces are equal, a steady-state velocity is reached. Combining equations (2), (3), and (5) yields the following result for the steady-state velocity:

$$v = \sqrt{\frac{2(1-a)LB}{\rho_f A_f C_D}}\sqrt{\frac{P}{R}} = \sqrt{\frac{2(1-a)B}{\rho_f A_f C_D}}\sqrt[4]{\frac{LPA_W}{\rho_c}} \quad (6)$$

$$\propto \sqrt{\frac{B}{A_f C_D}}\sqrt[4]{LPA_W}$$

Equation (6) reveals how the velocity changes with the relevant design parameters. The available power is proportional to the area of the device. Considering a locomotive implant in the shape of a cube with side length L, velocity varies inversely to the $4^{th}$ root of L. This means the velocity is relatively insensitive to changes in size. The velocity also varies with the square root of the magnetic field, which means it is relatively insensitive to the magnetic field as well.

As previously mentioned, the above result is not valid for small Reynolds numbers. As the device is scaled down and the Reynolds number becomes small (less than 1), the fundamental fluid behavior follows Stokes Law. To greatly simplify the analysis, we will consider the behavior of a sphere even though this representation is not exact. For a sphere with radius r, the drag force in this regime is $$D_2 = 6\pi\mu r v \quad (7)$$

with $\mu$ representing fluid viscosity and v representing velocity as before. To apply this equation to the presented design, we can approximate that 2r is roughly equal to L. If this equation for drag is combined with equations (2) and (3), the following is obtained for the velocity in the fluid:

$$v = \frac{(1-a)LB}{3\pi\mu L}\sqrt{\frac{P}{R}} = \frac{(1-a)B}{3\pi\mu}\sqrt{\frac{PA_W}{L\rho_c}} \quad (8)$$

$$\propto B\sqrt{\frac{PA_W}{L}}$$

In equation (8), we see that the variation of velocity with the relevant design parameters has fundamentally changed. Again, the available power is proportional to area, so the velocity varies with the square root of L, making it much more sensitive to size compared with the high Reynolds prediction. Also, velocity now decreases as size decreases. The magnetic field is directly proportional to the velocity, which shows that there is increased sensitivity to the field as well. It is important to note that neither equation (5) or (7) is valid when the Reynolds number does not fall into one of these extremes, and there is a transition period in between.

Figure 7:
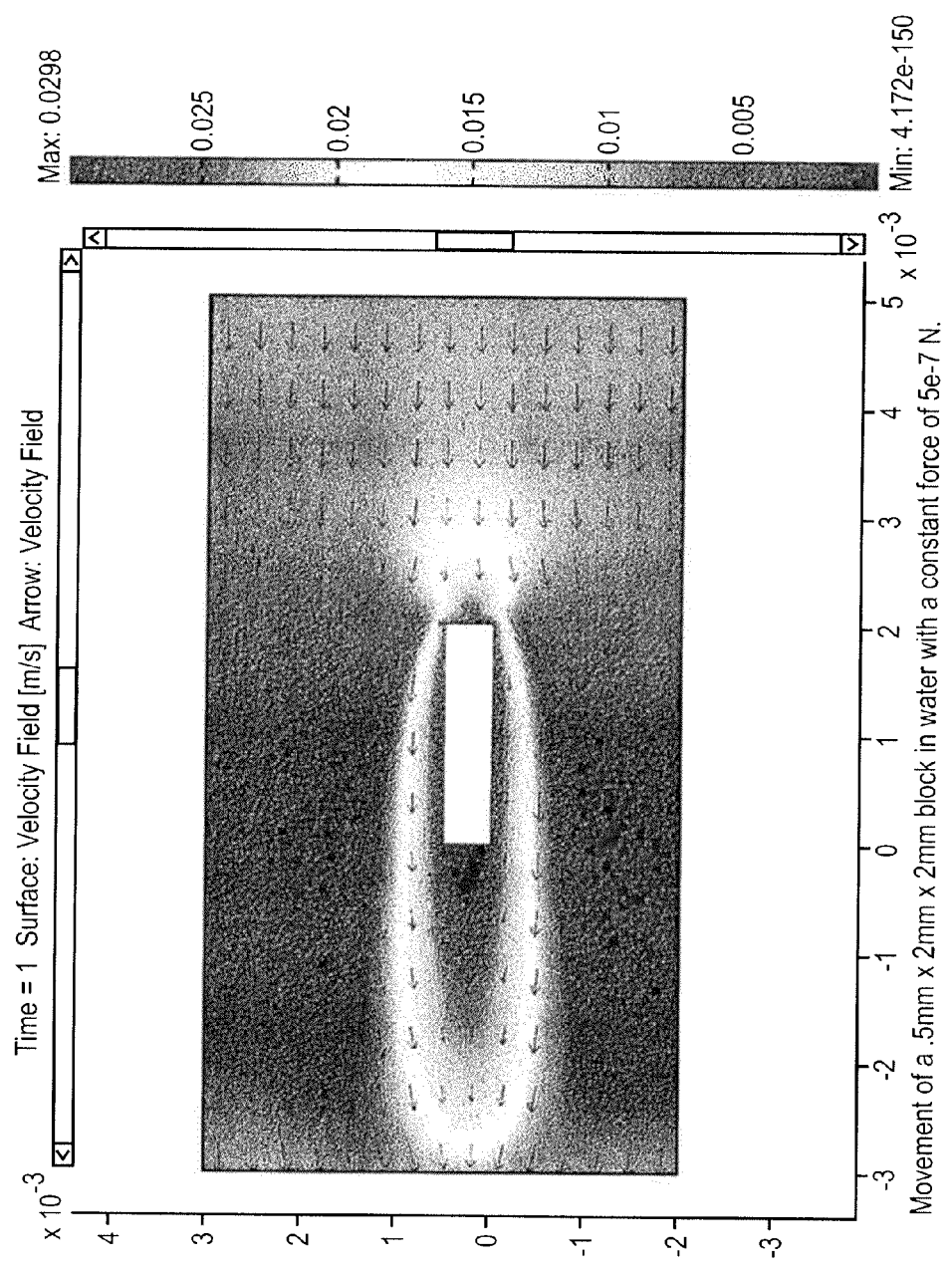
FIG. 7 illustrates a simulation of the locomotive implant.
Figure 8:
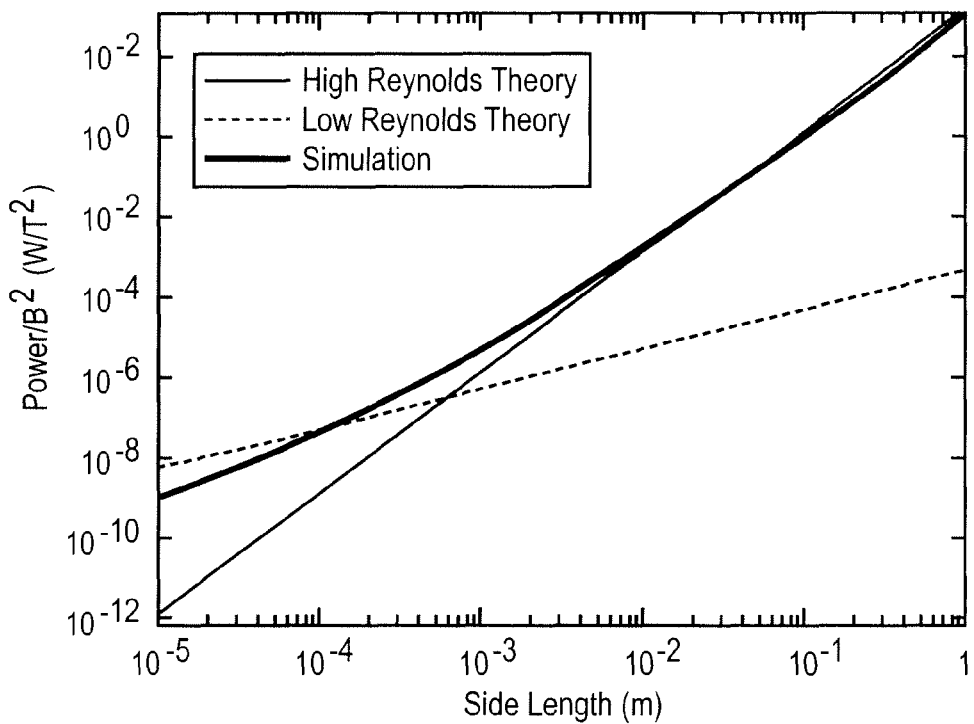
FIG. 8 is a graph for a simulated implant showing required power as a function of magnetic field and size.

The above simplification does not accurately describe the fluid dynamics in the transition region between high and low Reynolds numbers. Simulations of a locomotive implant approximated as a cube with side length L, and the drag force at a fixed velocity of 3 cm/sec were determined. This was done by fixing the simulated object in space in a section of moving fluid, and then measuring the forces exerted on the object, as shown in FIG. 7. The necessary power to supply this force with equations (2) and (3) was computed, and the plot shown in FIG. 8 shows the theoretical power versus size at 3 cm/sec based on both the high and low Reynolds theory, as well as the result of the simulations. In this plot, the power is normalized to magnetic field squared. For the theoretical predictions, the drag coefficient $C_D$ was assumed to be a constant equal to 1.05 for a cube, which is true for large Reynolds numbers.

At large sizes (and high Reynolds numbers), the simulation matches the predicted values very well. As the size of the locomotive implant 200 is reduced, the transition to the low Reynolds number prediction occurs. Since this prediction describes a sphere, there is some deviation, as predicted. Additionally, since $C_D$ varies inversely with the Reynolds number and this was not included in the simulation, this difference exists as well.

It will be understood, however, that the sizes of interest for medical locomotive implants 200 are at or below the transition region, and these simulations accurately predict their behavior.

Figure 9:
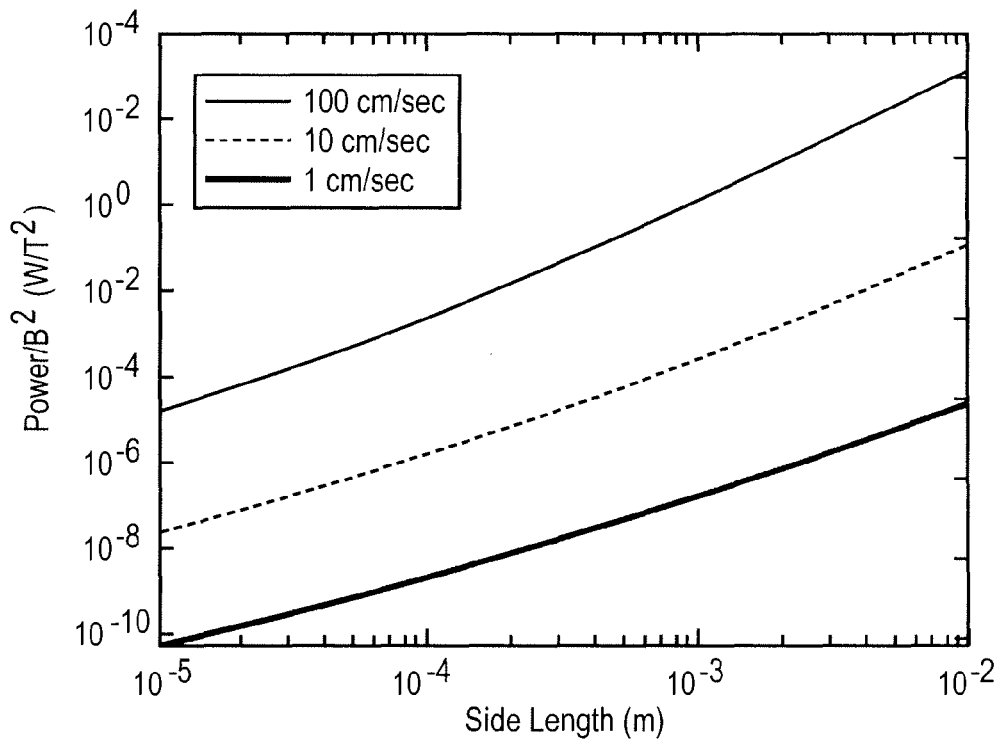
FIG. 9 is a graph for a simulated implant showing required power for different velocities.

In the design of the system 100 shown in FIG. 1, limits of performance are determined by the available power and the external magnetic field. The size of the locomotive implant 200 determines how much power can be received from the external power source 150, and the magnetic field depends only on the external magnetic field generator 160. Because different applications have different requirements, it is of interest to determine certain design limits. Using fluid simulations, as shown in FIG. 9, there is shown power as a function of the magnetic field and size at fixed velocities. The available power for a locomotive implant 200 can be estimated once its size and depth are known, and then the achievable velocity can be estimated with FIG. 9. As a simple example, consider the 1-mm cube analyzed above. At a depth of 2 cm, the available power is 150 µW. If a constant background field of 1 T is used, then to move at a speed of 1 cm/s, the force generating wire requires approximately 0.2 µW. There will many wire arrangements on the device, and the total power used by the propulsion system is the sum of the power used by these wires. A conservative estimate predicts that the required power is less than 10 µW, which is well within the power budget. The remaining power can be used for other components on the device, such as an application specific payload.

With the above description in mind, FIGS. 4(a)-(d) illustrate different current directions and corresponding force movement directions for a representative magnetic field used in embodiments described herein. These different current directions and corresponding force movement directions can be implemented in a locomotive implant device 200 as multiple different conductors 240, which together can provide for fine movement.

Referenced previously was also the payload 250 shown in FIG. 2. While there need not be any payload, in certain embodiments the payload 250 can be a sensor, such as a temperature monitor, a pressure sensor, a pH sensor, a chemical sensor, an image sensor based upon light, ultrasound, or some other characteristic. They payload 250 can also be an actuator or a stimulator. The payload 250 can also include a heat mechanism, which can then heat to remove an associated cover (preferably made with the same material as the encapsulant, though other materials can be used), and thereby dispense with a medication type disposed within the locomotive implant 200 at a precise location based upon the removal of the cover using the generated heat.

Thus, for one application using the locomotive implant 200, would be to deliver drugs to a specific area in the GI tract over a longer period of time than is possible with pills. For example, local treatment of inflammatory bowel disease, where the implant can be made to stay in a relatively stable position in the bowel by active locomotion, is possible for the delivery of drugs over hours or days. This same principle applies to the local administration of chemotherapy for tumors inside the GI tract, as well as drug delivery to the blood stream. Also active ejection can be implemented so drugs are delivered very quickly but to a specific location.

Figure 5A:
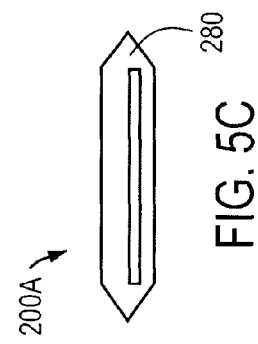
FIGS. 5(a)-5(c) illustrate side, top, and cross section views of one embodiment of a locomotive implant.
Figure 5B:
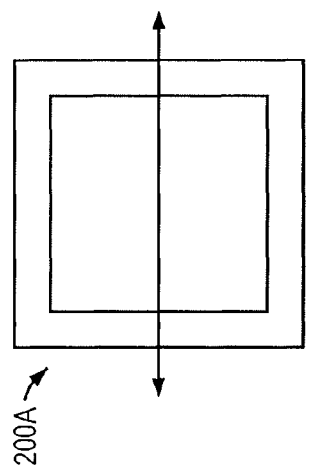
Figure 5C:
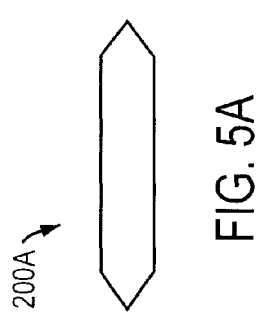

FIGS. 5(a)-5(c) illustrate side, top, and cross section views of one embodiment 200A of a locomotive implant. As shown, locomotive implant 200A has generally a square shape to the exterior capsule body, with each of the edges being beveled so as to form a point at each edge surface, which thereby has a more aerodynamic shape. Within the locomotive implant 200A is a substrate 270 on which the various components previously described with respect to FIG. 2 are formed.

Figure 6A:
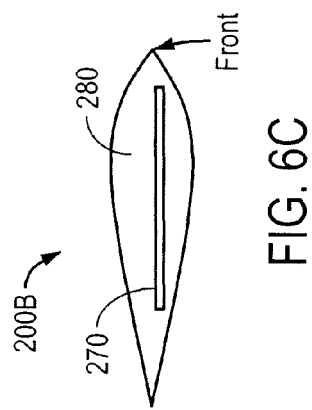
FIGS. 6(a)-6(c) illustrate side, top, and cross section views of one embodiment of a locomotive implant.
Figure 6B:
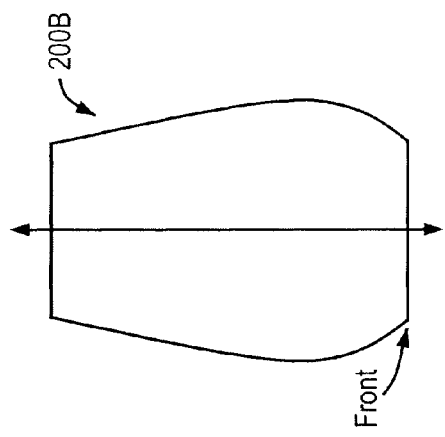
Figure 6C:
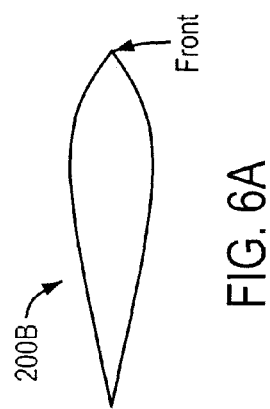

FIGS. 6(a)-6(c) illustrate side, top, and cross section views of one embodiment 200B of a locomotive implant 200. As shown, locomotive implant 200B has generally a teardrop shape to the exterior capsule body, with each of the edges being rounded so as to form a point at each edge surface, which thereby has a more aerodynamic shape. Within the locomotive implant 200B is a substrate 270 on which the various components previously described with respect to FIG. 2 are formed.

In manufacture, the locomotive implant circuit 210 is preferably formed on a single substrate, which can be a substrate with circuits thereon, including wire traces or wire loop traces for the conductors 240, or alternately silicon on chip (SOC) structures. Surrounding the substrate 270 with the locomotive implant circuit 210 disposed thereon is an encapsulant material 280, such as a biocompatible plastic like polyvinylchloride (PVC), polytetrafluoroethylene (PTFE) or silicone which protects the circuit 210 therein. It is noted that whether a single antenna is used (if control signals are superimposed within wireless power signals), or multiple antennas are used to separate the wireless power and the implant control signals, the antennas can be configured with respect to the encapsulant material 280 to properly perform.

Figure 10:
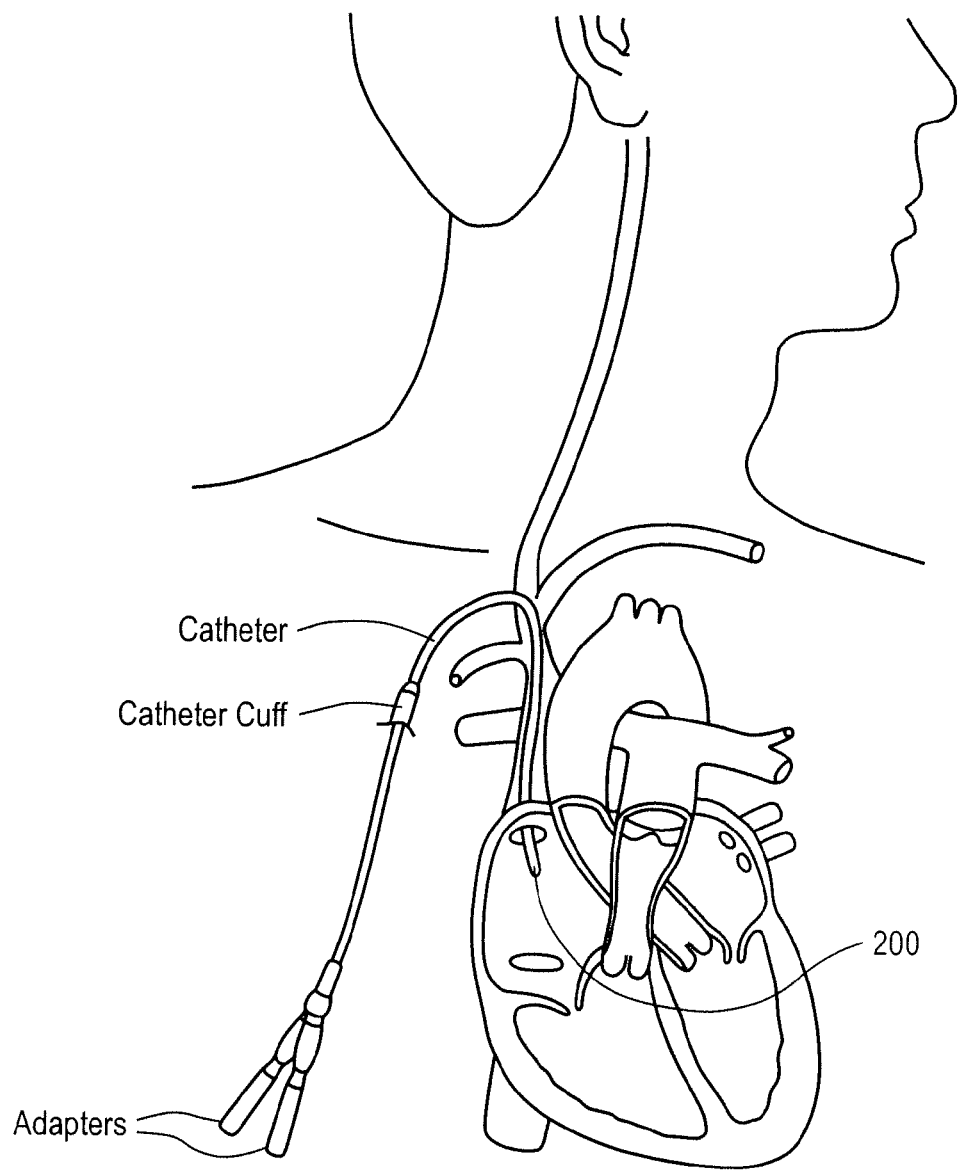
FIG. 10 illustrates an embodiment of the locomotive implant fastened to another insertable device.

FIG. 10 illustrates an embodiment of the locomotive implant 200 fastened to another insertable device 400. In particular, this implementation preferably uses wired power, and as such the wireless power receiver becomes the wire as discussed above. Fine precision control of the other insertable device 400, such as a catheter, allows for precision control of a tip 410 of the catheter 400, and the locomotive implant is positioned toward the tip to allow for control thereof, without interfering with, for example, laser light used for ablation or other sensory light that is transmitted from and/or received by the other insertable device 400.

A particular application of the implant system 100 is to enable capsule endoscopy with active movement capabilities. Conventional clinical capsule endoscopy products are passive, with motion driven by the natural GI peristalsis and therefore effectiveness depends on the random accumulation of images during the 8-24 hours that the capsule passes through the GI tract. A major limitation is that the capsule may not be oriented properly in a particular location to "see" a tumor. Since the movement of the capsule is not controllable, extended observation of interested spots along the GI tract is impossible. This application, and some of the others mentioned below, may require a "charging" device. Since the power continuously delivered to the implant may not be high enough to provide, e.g., illumination for imaging. A charging device, such as a capacitor, can accumulate the power over time and deliver a higher power when illumination is needed.

The locomotive implant system 100 described herein will enable externally controlled movement of the capsule (as the capsule becomes the locomotive implant 200), and reduces the time for the procedure and improves the accuracy of diagnosis, since the operator can drive the capsule to the areas of interest and perform careful examination of suspicious areas with optimal views. The procedure would be completed in time comparable to a regular endoscopy, in a matter of 30 minutes to an hour. In addition, the size of conventional capsules are around a couple of centimeters, with about half of the space is occupied by battery. The proposed power delivery system can reduce the size of the capsule by half. A further advantage of using locomotive implant capsule is that it can perform GI tract examinations without a full bowel prep, which is highly unpleasant for patients, by being able to navigate the locomotive implant adjacent to the wall underneath any material in the bowel.

The locomotive implant system 100 described herein also has numerous surgical applications, including assisting with surgery within the abdomen without having to displace the bowel, or minimally-invasive dissection procedures for grafting. Since the locomotive implant 200 is also a power source, besides facilitating drug delivery, cutting, ablation, and suturing during surgery, these implants 200 can also be used as small light sources to give optimal illumination for the surgeon to navigate around specific locations of interest (this application will require the charging device mentioned earlier). With external motion control, the implants can be driven to different areas and oriented for better visualization.

As is shown by the above, depending upon the payload 250, the same structure can be used to implement a number of different purposes.

As also apparent, the locomotive implant 200 can create a force within fluid environments of liquids as well as gases. Thus, within a GI tract, or with the vascular space, particularly the venous system, control of the locomotive implant 200 is akin to a submersible vessel. Within a fluid gaseous environment, such as within a lung, typically the locomotive implant 200 will require affixation to another device, and provide fine control of another device that can support the implant within a particular point within a particular plane of the fluid gaseous environment.

Although the present invention has been particularly described with reference to embodiments thereof, it should be readily apparent to those of ordinary skill in the art that various changes, modifications and substitutes are intended within the form and details thereof, without departing from the spirit and scope of the invention. Accordingly, it will be appreciated that in numerous instances some features of the invention will be employed without a corresponding use of other features. Further, those skilled in the art will understand that variations can be made in the number and arrangement of components illustrated in the above figures. It is intended that the scope of the appended claims include such changes and modifications.

What is claimed is:

1. A locomotive implant for usage within a predetermined magnetic field comprising:
a body;
a source of power disposed on or within the body;
a plurality of switchable conductors arranged in a predetermined pattern on or within the body, each of the switchable conductors adapted to pass a current obtained from the source of power along a forward path to thereby create, in the presence of the predetermined magnetic field, a force that directly propels the locomotive implant, wherein the locomotive implant is directly propelled without using any moving parts to obtain propulsion; and
a controller disposed on or within the body and adapted to receive directional control signals and to control the current in the switchable conductors using the directional control signals.

2. The locomotive implant according to claim 1 wherein the directional control signals are used to provide direct steering forces that cause steering of the locomotive implant.

3. The locomotive implant according to claim 1 wherein a direction of motion of the locomotive implant is changed by fluid drag forces.

4. The locomotive implant according to claim 1 wherein a direction of motion of the locomotive implant is changed by using torques from loops of wire disposed on or within the locomotive implant.

5. The locomotive implant according to claim 1 wherein the source of power is one of a wireless power receiver and a wire connected to a power source.

6. The locomotive implant according to claim 1 wherein the body is a capsule body, and wherein the source of power, the plurality of switchable conductors and the controller are disposed within the capsule body.

7. The locomotive implant according to claim 6 wherein the locomotive implant is mm sized.

8. The locomotive implant according to claim 7 wherein the directional control signals are used to provide direct steering forces that cause steering of the locomotive implant.

9. The locomotive implant according to claim 7 wherein a direction of motion of the locomotive implant is changed by fluid drag forces.

10. The locomotive implant according to claim 7 wherein a direction of motion of the locomotive implant is changed by using torques from loops of wire disposed on or within the locomotive implant.

11. The locomotive implant according to claim 6 wherein the directional control signals are used to provide direct steering forces that cause steering of the locomotive implant.

12. The locomotive implant according to claim 6 wherein a direction of motion of the locomotive implant is changed by fluid drag forces.

13. The locomotive implant according to claim 6 wherein a direction of motion of the locomotive implant is changed by using torques from loops of wire disposed on or within the locomotive implant.

14. The locomotive implant according to claim 6 wherein the locomotive implant is sub-mm sized.

15. The locomotive implant according to claim 14 wherein the directional control signals are used to provide direct steering forces that cause steering of the locomotive implant.

16. The locomotive implant according to claim 1 wherein the body is fastened to an insertable device.

17. The locomotive implant according to claim 16 wherein a direction of motion of the locomotive implant is changed by fluid drag forces.

18. The locomotive implant according to claim 16 wherein a direction of motion of the locomotive implant is changed by using torques from loops of wire disposed on or within the locomotive implant.

19. The locomotive implant according to claim 16 wherein the insertable device is a catheter.

20. The locomotive implant according to claim 19 wherein the directional control signals are used to provide direct steering forces that cause steering of the locomotive implant.

21. The locomotive implant according to claim 1 wherein the plurality of switchable conductors provide for a plurality of redundant switchable conductor combinations that each provide a substantially equivalent force.

22. The locomotive implant according to claim 1 wherein the locomotive implant is mm sized.

23. The locomotive implant according to claim 1 wherein the locomotive implant is sub-mm sized.

\* \* \* \* \*